(12) United States Patent
Weedon

(10) Patent No.: US 7,249,507 B2
(45) Date of Patent: Jul. 31, 2007

(54) FLUID LEVEL SENSOR PROBE

(75) Inventor: Thomas C. Weedon, Belleville, MI (US)

(73) Assignee: Automotive Components Holdings, LLC, Dearborn, MI (US)

( * ) Notice: Subject to any disclaimer, the term of this patent is extended or adjusted under 35 U.S.C. 154(b) by 165 days.

(21) Appl. No.: 10/996,555

(22) Filed: Nov. 23, 2004

(65) Prior Publication Data

US 2006/0107737 A1    May 25, 2006

(51) Int. Cl.
*G01F 23/24* (2006.01)
(52) U.S. Cl. .................................. 73/304 R
(58) Field of Classification Search .............. 73/304 R
See application file for complete search history.

(56) References Cited

U.S. PATENT DOCUMENTS

| | | | |
|---|---|---|---|
| 4,594,892 A | 6/1986 | Asmundsson | |
| 4,610,165 A | 9/1986 | Duffy et al. | |
| 4,855,706 A * | 8/1989 | Hauptly | ............... 338/34 |
| 4,982,606 A | 1/1991 | Adamski et al. | |
| 4,988,975 A | 1/1991 | Nap | |
| 5,005,409 A | 4/1991 | Hochstein | |
| 5,052,223 A | 10/1991 | Regnault et al. | |
| 5,097,703 A | 3/1992 | Peter | |
| 5,861,811 A | 1/1999 | Lease et al. | |
| 5,969,620 A * | 10/1999 | Okulov | .................... 340/620 |
| 6,571,625 B2 | 6/2003 | Thomson | |
| 6,624,755 B1 | 9/2003 | Chamberlin | |
| 6,675,989 B1 | 1/2004 | Ritter et al. | |
| 6,766,703 B1 | 7/2004 | Kluth et al. | |
| 2004/0007061 A1 | 1/2004 | Forgue | |

* cited by examiner

*Primary Examiner*—Hezron Williams
*Assistant Examiner*—Paul M West
(74) *Attorney, Agent, or Firm*—MacMillan, Sobanski & Todd, LLC

(57) ABSTRACT

A fluid level sensor probe is provided. The fluid level sensor probe includes a housing, a first and second electrode, and an electric circuit. The first electrode is located on a first surface of the housing. A second surface of the housing is located adjacent the first surface and forms an angle with the second surface of about 90° or less. The first and second electrode are substantially flush with the housing. Further, the size of the first surface and angle between the first and second surface is configured to prevent a contiguous fluid droplet from forming across the first and second electrode.

17 Claims, 2 Drawing Sheets

FLUID LEVEL SENSOR PROBE

BACKGROUND

1. Field of the Invention

The present invention generally relates to a fluid level sensor probe.

2. Description of Related Art

Typically, electronic fluid level sensor probes include two dual electrodes that are immersed in fluid. The sensor acts like an electronic switch. As such, the switch provides either an open or closed output when submersed in the fluid. If the fluid level is such that a contiguous path of fluid contacts both probes and, therefore, allows current to flow between the two probes through the fluid, then an electronic circuit sends a signal indicating fluid is present based on the electrically closed circuit. Otherwise, the electronic fluid level sensor probe indicates no fluid is present, based on the electrically opened circuit.

One problem with currently existing probes is that fluid capillary action causes a bubble or droplet to remain contiguous across the probes and, therefore, a conductive path across the probe contacts for upwards of fifteen to twenty minutes after the probe is no longer immersed in the fluid.

In view of the above, it is apparent that there exists a need for an improved fluid level sensor probe.

SUMMARY

In satisfying the above need, as well as overcoming the enumerated drawbacks and other limitations of the related art, the present invention provides an improved fluid level sensor probe.

The fluid level sensor probe includes a housing, a first electrode, second electrode, and an electric circuit. The first electrode is located on a first surface of the housing. A second surface of the housing is located adjacent the first surface and forms an angle with the second surface of about 90° or less. The first and second electrodes are substantially flush with the housing. Further, the size of the first surface and the angle between the first and second surfaces is configured to prevent a contiguous fluid droplet from forming across the first and second electrodes.

The housing is generally cylindrical in shape and a boss extends from an end of the housing. The first electrode is located at a center of the boss. The second electrode forms a generally circular shape, substantially flush with the end of the housing and circumscribes the boss.

The first and second electrode are in electrical communication with an electrical circuit that detects current flow between the first and second electrodes. Further, the electric circuit is located in a cavity formed by the housing of the fluid level sensor probe.

Further objects, features and advantages of this invention will become readily apparent to persons skilled in the art after a review of the following description, with reference to the drawings and claims that are appended to and form a part of this specification.

DETAILED DESCRIPTION

Figure 1:
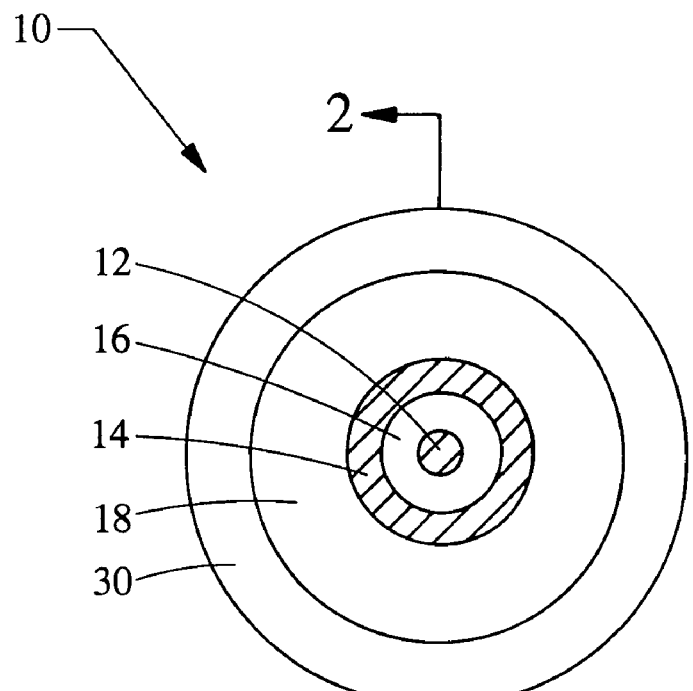
FIG. 1 is a top view of a fluid level sensor probe in accordance with the present invention.
Figure 2:
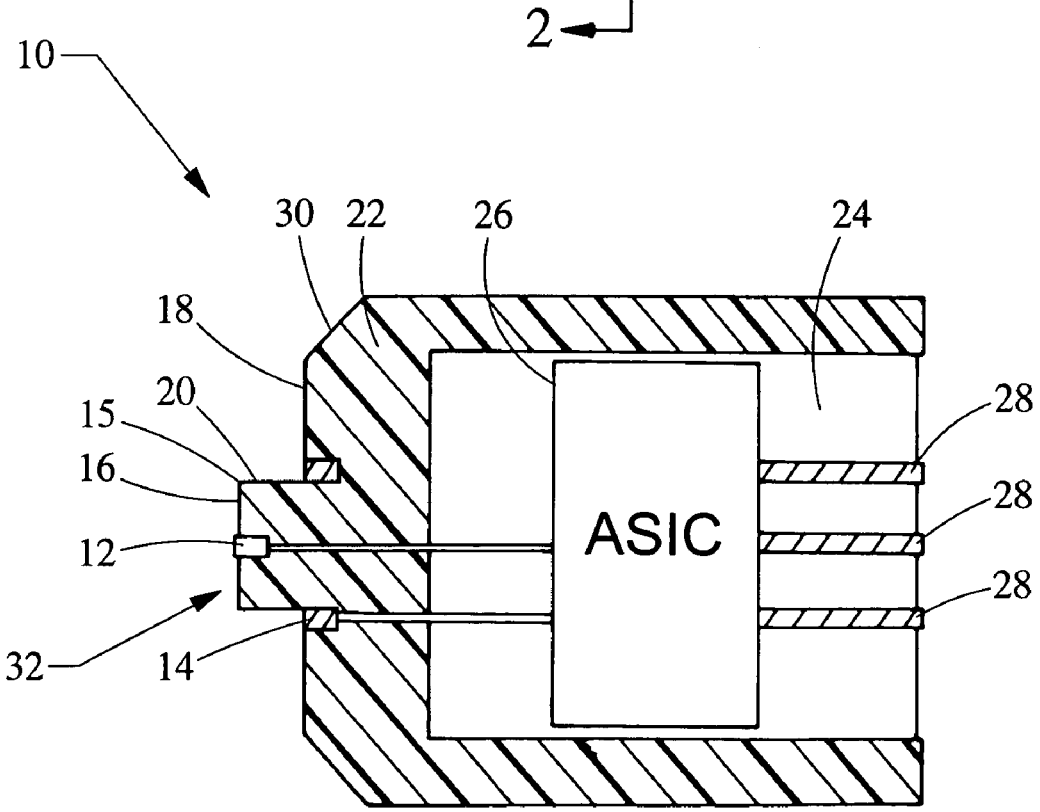
FIG. 2 is a cutaway side view, generally taken along line 2-2 of FIG. 1, of a fluid sensor probe in accordance with the present invention.

Referring now to FIGS. 1 and 2, a fluid level sensor probe embodying the principles of the present invention is illustrated therein and designated at 10. The fluid level sensor probe 10 includes a first electrode 12, a second electrode 14, a housing 22, and an electrical circuit 26. Both the first and second electrodes 12, 14 are in electrical communication with the electric circuit 26, which causes a voltage to be provided across the first and second electrodes 12, 14 allowing a conduction of electric current between the first and second electrodes 12, 14, when the fluid level sensor probe 10 is immersed in an electrically conductive fluid.

The housing 22 includes a chamfer 30 for ease of insertion into a fluid tank. The housing 22 has a generally cylindrical shape, with first and second surfaces 16, 20 forming a generally cylindrical boss or platform 32 extending from a third surface 18 defining the end of the housing 22. The first and second electrode 12, 14 are two metallic bodies, the exterior surfaces of which are flush or nearly flush with the exterior surface of the housing 22. Accordingly, the housing 22 is made of a non-conductive material, such as a plastic, to electrically isolate the first and second electrodes 12, 14. The first electrode 12 is provided on the first surface 16 of the housing 22 while the second electrode 14 is provided on the third surface 18 of the housing 22. The first surface 16 is oriented with relation to the second surface 20 to form an angle with the second surface 20 of about 90° or less. Oriented in this way, the first and second surfaces 16, 20 of the housing 22 are configured to inhibit a drop of fluid from forming across the first and second electrodes 12, 14 thereby preventing an electrical connection between the first and second electrodes 12, 14 after the fluid sensor probe is no longer immersed in the fluid. The angle of the first surface 16 relative to the second surface 20 and the size of the first surface 16 is calculated in relation to the surface tension/cohesion, the atmospheric pressure, and the temperature of the fluid to isolate the first and second electrodes 12, 14 after their removal from the fluid. In addition, the spacing of the first electrode 12 relative to edge 15 of the first surface 16 and the spacing of the second electrode 14 relative to edge 15 are also configured to prevent a drop from forming across the first and second electrodes 12, 14.

Preferably, the first electrode 12 has a generally circular shape and the second electrode 14 has a generally annular shape concentric with the cylindrical platform 32 and the first electrode 12. The distance between the first and second electrode 12, 14 are greater than the maximum possible fluid droplet size. The following calculations demonstrate a determination of this distance for the smallest probe design.

Determining the maximum size of the fluid droplet is dependent on the capillary adhesion of the fluid, which is defined by the equation:

$$F = \delta \pi D$$

Where F equals the total force of the adhesion of the drop to the surface because of surface tension; $\delta$ equals surface tension of the fluid at a given temperature and atmospheric pressure (water is 72 dynes/cm @25 deg F.); and D is the diameter of the sensor.

The expression $\pi D$ defines the circumference of the droplet. The capilliary adhesion is strongest along the perimeter of the droplet.

The weight of the fluid droplet must be defined because, when the weight of the bubble exceeds the surface tension, the bubble of fluid will divide. The weight of the fluid is the droplet volume (V) times the specific gravity (S) of the fluid at a given temperature and atmospheric pressure. Therefore, the weight can be represented by the general equation; W=V×S. The volume V is represented by V=(2/3)πH(D/2)² where H is the height of the droplet. In order to prevent a droplet from clinging to the sensor and shorting out the two electrodes, the weight of the drop must be greater than the surface tension can hold, or W>F. It is possible to calculate the smallest acceptable probe diameter from these equations for a given fluid. With these expressions, it is possible to calculate the minimum diameter of the first surface 16, or the maximum size of a droplet for a given fluid, thereby preventing capillary action from shorting out the first and second electrode 12, 14. The sharp edge on the boss or platform 32 surrounding the first electrode 12 breaks the surface tension or capillary adhesion and the first surface 16 cannot support a fluid drop that would provide an electrical path between the first and second electrodes 12, 14.

The electronic circuit 26 is located in a cavity 24 formed by walls of the housing 22. The electronic circuit 26 is shown as an integrated circuit package with connections 28 extending therefrom to communicate with a vehicle controller.

Figure 3:
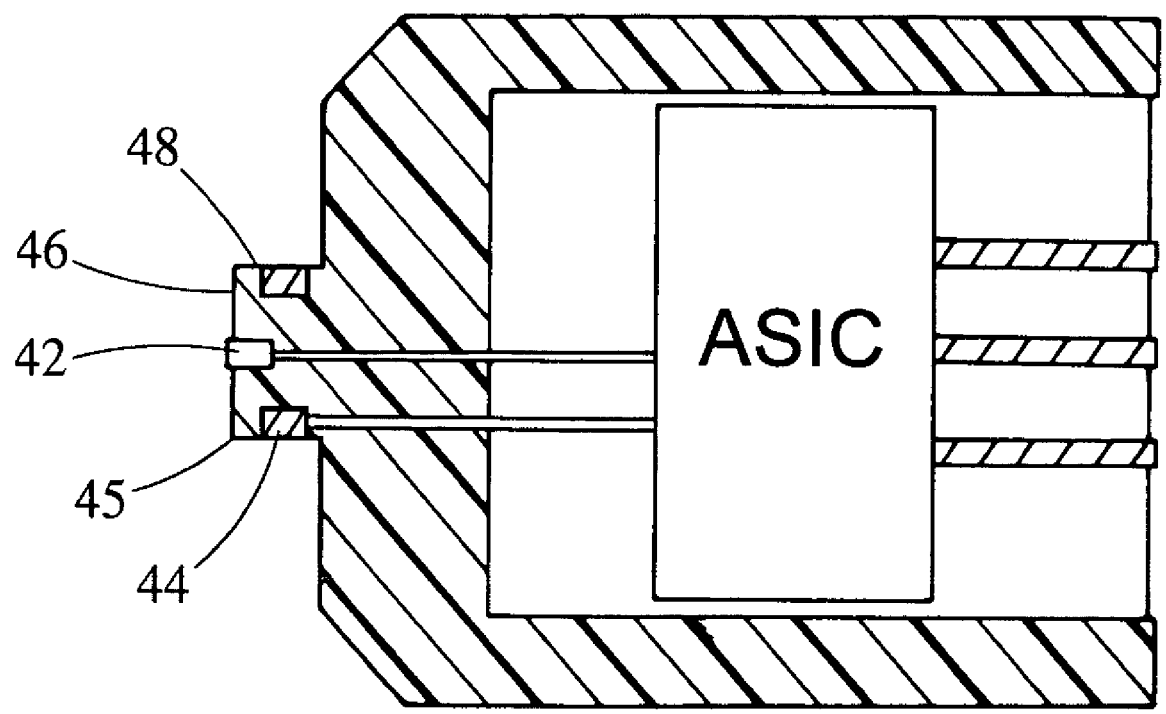
FIG. 3 is a cutaway side view of another embodiment of a fluid sensor probe in accordance with the present invention.

In an alternative configuration shown in FIG. 3, the first electrode is located in the center of the platform 32, as previously discussed, while the second electrode is located in the side wall of the platform. As such, the first and second surface 46, 48 may share an edge 45. The distance of the first and second electrode 42, 44 from the edge 45 and the angle of the first surface 46 relative to the second surface 48 prevent a drop from forming across the first and second electrodes 42, 44. Therefore, the first and second surface 46, 48 form an angle of about 90° or less. As in the previous embodiment, first electrode 42 is generally flush with the first surface 46 and the second electrode 44 is generally flush with the second surface. If a drop should form across the top or on the end, it would not be able to provide an electrical path from the first electrode 42 through the fluid to the second electrode 44 on the side of the cylinder if the diameter and height of the cylindrical platform formed by the first and second surface 46, 48 are bigger than the dimensions calculated previously to prevent a drop of fluid from shorting out the first and second electrode 42, 44. Other structural elements shown are similar in relation to the previous embodiment.

As a person skilled in the art will readily appreciate, the above description is meant as an illustration of implementation of the principles this invention. This description is not intended to limit the scope or application of this invention in that the invention is susceptible to modification, variation and change, without departing from spirit of this invention, as defined in the following claims.

I claim:

1. A fluid level sensor probe comprising:
   a non-conductive housing having a first exterior surface at a distal end of the housing and a second exterior surface non-coplanar with the first exterior surface and spaced from the distal end;
   a first embedded electrode exposed at the first exterior surface of the housing; and
   a second embedded electrode exposed at other than the first exterior surface;
   wherein the first exterior surface is adjacent the second exterior surface and forms an angle with the second exterior surface of about 90° or less to prevent a contiguous fluid droplet from forming across the first and second electrode.

2. The fluid level sensor probe of claim 1, wherein the the second electrode is exposed at the second exterior surface.

3. The fluid level sensor probe according to claim 1, wherein the first and second electrode is in electrical communication with an electrical circuit.

4. The fluid level sensor probe according to claim 3, wherein the electrical circuit detects current flow between the first and second electrodes.

5. The fluid level sensor probe according to claim 3, wherein the housing forms a cavity and the electric circuit is located within the cavity.

6. The fluid level sensor probe according to claim 1, wherein the distance between the first and second electrode is based on the surface tension of the fluid.

7. The fluid level sensor probe according to claim 1, wherein the distance between the first and second electrode is based on the atmospheric pressure of the fluid.

8. The fluid level sensor probe according to claim 1, wherein the distance between the first and second electrode is based on the temperature of the fluid.

9. The fluid level sensor probe according to claim 1, wherein the distance between the first and second electrode is based on the relationship W>F; where W is the weight of a maximum size droplet formed on the first surface, and F is the surface tension of a maximum size droplet formed on the first surface.

10. The fluid level sensor probe according to claim 1, wherein the housing is generally cylindrical in shape.

11. The fluid level sensor probe according to claim 1, wherein housing has a third exterior surface oriented substantially parallel to the first exterior surface, and wherein the second electrode is exposed at the third exterior surface.

12. The fluid level sensor probe according to claim 11, wherein the second electrode is flush with the third exterior surface.

13. The fluid level sensor probe according to claim 12, wherein the first and second exterior surface of the housing form a generally cylindrical platform extending from the third exterior surface of the housing.

14. The fluid level sensor probe according to claim 13, wherein the first electrode is located at the center of the generally cylindrical platform.

15. The fluid level sensor probe according to claim 14, wherein the second electrode forms a generally circular shape and is concentric with the generally cylindrical platform.

16. The fluid level sensor probe according to claim 1, wherein the first and second exterior surfaces of the housing are connected at a first edge.

17. The fluid level sensor probe according to claim 16, wherein the second electrode is flush with the second exterior surface of the housing.

* * * * *